(12) United States Patent
Dmitrovsky et al.

(10) Patent No.: US 7,586,022 B2
(45) Date of Patent: Sep. 8, 2009

(54) TRANSGENIC NON-HUMAN ANIMAL MODEL OF LUNG TUMORIGENESIS

(75) Inventors: Ethan Dmitrovsky, Hanover, NH (US); Yan Ma, Beverly, MA (US); Sarah J. Freemantle, Hanover, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 11/996,003

(22) PCT Filed: Jul. 28, 2006

(86) PCT No.: PCT/US2006/029229
§ 371 (c)(1),
(2), (4) Date: Jan. 17, 2008

(87) PCT Pub. No.: WO2007/016263
PCT Pub. Date: Feb. 8, 2007

(65) Prior Publication Data
US 2008/0313750 A1 Dec. 18, 2008

(51) Int. Cl.
*A01K 67/027* (2006.01)
*A01K 67/00* (2006.01)
*A01K 67/033* (2006.01)
*G01N 33/00* (2006.01)

(52) U.S. Cl. .................. 800/18; 800/3; 800/8; 435/325

(58) Field of Classification Search ................ 800/3, 800/8, 18; 435/320.1, 325
See application file for complete search history.

(56) References Cited

U.S. PATENT DOCUMENTS

2003/0224993 A1  12/2003  Land et al. ................. 514/12

OTHER PUBLICATIONS

MGI website labeled Ccne1, 2009.*
Wagner (May 1995, Clin. And Experimental Hypertension, vol. 17, pp. 593-605).*
Mullins (1996, J. Clin. Invest., vol. 98, 1557-1560).*
Wall (1996, Theriogenology, vol. 45, p. 57-68).*
Karsunky (Oncogene, 1999, vol. 18, p. 7816-7824).*
Borok et al., "Differential Regulation of Rat Aquaporin-5 Promoter/Enchancer Activities in Lung and Salivary Epithelial Cells", J. Biol. Chem. 2000 275(34):26507-26514.
Cassia et al., "Cyclin E gene (CCNE) amplification and hCDC4 mutations in endometrial carcinoma", J Pathol 2003 201:589-595.
Dosaka-Akita et al., "A Risk-Stratification Model of Non-Small Cell Lung Cancers Using Cyclin E, Ki-67, and *ras* p21:Different Roles of G1 Cyclins in Cell Proliferation and Prognosis", Cancer Research 2001 61:2500-2504.
Dragnev et al., "Specific Chemopreventive Agents Trigger Proteasomal Degradation of $G_1$ Cyclins: Implications for Combination Therapy", Clinical Cancer Research 2004 2570 (10):2570-2577.
Duan et al., "Lung-specific expression of human mutant p53-273H is associated with high frequency of lung adenocarcinoma in transgenic mice", Oncogene 2002 21:7831-7838.
Ehrhardt et al., "Development of pulmonary bronchiolo-alveolar adenocarcinomas in transgenic mice overexpressing murine c-myc and epidermal growth factor in alveolar type II pneumocytes", British Journal of Cancer 2001 84 (6):813-818.

Fukuse et al., "Prognostic Significance of Cyclin E Overexpression in Resected Non-Small Cell Lung Cancer", Cancer Research 2000 60:242-244.
Geisen et al., "Loss of $p27^{kip1}$ cooperates with cyclin E in T-cell lymphomagenesis", Oncogene 2003 22:1724-1729.
Glasser et al., "Genetic element from human surfactant protein SP-C gene confers bronchiolar-alveolar cell specificity in transgenic mice", Am J Physiol 1991 261:L349-L356.
Graham et al., "Sensory nerves Promote Ozone-induced Lung Inflammation in Mice", Am J Respir Crit Care Med 2001 164 :307-313.
Koff et al., "Human Cyclin E, a New Cyclin That Interacts with Two Members of the CDC2 Gene Family", Cell 1991 66:1217-1228.
Langenfeld et al., "Inhibited transformation of immortalized human bronchial epithelial cells by retinoic acid is linked to cyclin E down-regulation", Oncogene 1996 13 :1983-1990.
Lonardo et al., "Overexpression of Cyclins D1 and E Is Frequent in Bronchial Preneoplasia and Precedes Squamos Cell Carcinoma Development", Cancer Research 1999 59:2470-2476.
Miller-Tidow et al., "Cyclin E is the Only Cyclin-dependent Kinase 2-associated Cyclin that Predicts Metastasis and Survival in Early Stage Non-Small Cell Lung Cancer", Cancer Research 2001 61:647-653.
Nakayama et al., "Targeted Disruption of Skp2 Results in Accumulation of Cyclin E and $p27^{kip1}$, Polyploidy and Centrosome Overduplication", The EMBO Journal 2000 19 (9) :2069-2081.
Palmarini et al., "The Long Terminal Repeat of Jaagsiekte Sheep Retrovirus is Preferentially Action in Differentiated Epithelial Cells of the Lungs", J Virology 2000 74 (13) :5776-5787.
Schraml et al., "Cyclin E Overexpression and Amplification in Human Tumours", J Pathology 2003 200:375-382.
Sewing et al., "Alternative Splicing of Human Cyclin E", J Cell Science 1994 107:581-588.
Spruck et al., "Deregulated Cyclin E Induces Chromosome Instability", nature 1999 401:297-300.
Strohmaier et al., "Human F-box Protein hCdc4 Targets Cyclin E for Proteolysis and Is Mutated in a Breast Cancer Cell Line", Nature 2001 413:316-322.
NCBI Accession No. NM_057749 [gi:17318564] with Revision History Dec. 4, 2001-Sep. 3, 2005.
NCBI Accession No. NM_057735 [gi:17318562] with Revision History Dec. 4, 2001-Nov. 17, 2006.
NCBI Accession No. NM_004702 [gi:17318566] with Revision History May 7, 1999-May 14, 2005.
NCBI Accession No. NM_004702 [gi:17138566] with Revision History May 7, 1999-May 14, 2005.
NCBI Accession No. NM001238 [gi:17318558] with Revision History Dec. 4, 2001-Sep. 23, 2005.

* cited by examiner

*Primary Examiner*—Michael C. Wilson
(74) *Attorney, Agent, or Firm*—Licata & Tyrrell P.C.

(57) ABSTRACT

The present invention is a transgenic non-human animal whose genome contains a transgene containing a nucleic acid encoding a cyclin E protein operably linked to a regulatory element including a lung-specific promoter. The transgenic animals of the present invention have elevated levels cyclin E protein in the lung and have in increased occurrence of lung carcinogenesis. The animals of the instant invention were also found to have increased levels of Gli1 and Shh. Vectors, cells and cell lines are provided, as is a method for identifying a therapeutic agent for the chemoprevention or treatment of lung cancer.

6 Claims, No Drawings

TRANSGENIC NON-HUMAN ANIMAL MODEL OF LUNG TUMORIGENESIS

INTRODUCTION

This invention was supported in part by funds from the U.S. government (NIH Grant Nos. NIH RO1 CA87546, RO1 CA111422 and RO1 CA62275) and the U.S. government may therefore have certain rights in the invention.

BACKGROUND OF THE INVENTION

Cell cycle progression is controlled by cyclin-dependent kinases (Cdks), the activity of which is positively regulated by cyclins and negatively regulated by Cdk-inhibitors. In late G1 phase of the cell cycle, cyclin E achieves maximal expression level (Koff, et al. (1992) *Science* 257(5077):1689-94). Cyclin E binds to and activates cyclin-dependent kinase 2 (Cdk2) to promote G1/S transition (Koff, et al. (1992) supra). Cyclin E abundance and cyclin E-Cdk activity are each diminished at the G2/M phase. The amount and timing of cyclin E-Cdk2 activity are both precisely regulated to assure the normal progression of the cell cycle. Constitutive cyclin E overexpression shortens the G1 phase, impairs S-phase progression, and causes chromosomal instability (Ohtsubo, et al. (1995) *Mol. Cell Biol.* 15:2612-2624; Spruck, et al. (1999) *Nature* 401:297-300). In contrast, inhibition of cyclin E in G1 phase of the cell cycle blocks the occurrence of S-phase (Ohtsubo, et al. (1995) supra).

Cyclin E is regulated primarily at the levels of gene transcription and by ubiquitin-dependent proteolysis. Cyclin E is a transcriptional target of E2F family members, the function of which is repressed by association with the retinoblastoma (Rb) gene product. Phosphorylation of Rb by D-type cyclin-associated Cdk4/6 can release E2F thereby activating cyclin E expression (Coqueret (2002) *Gene* 299:35-55). Cul3 promotes ubiquitination of free cyclin E that is unbound to Cdk2 (Clurman, et al. (1996) *Genes Dev.* 10:1979-90; Singer, et al. (1999) *Genes Dev.* 13:2375-87). Ubiquitination of Cdk2 bound cyclin E is dependent on phosphorylation of threonine 380 (Won and Reed (1996) *EMBO J.* 15:4182-93) and threonine 62 (Strohmaier, et al. (2001) *Nature* 413(6853):316-22). Phosphorylation of these amino acids allows cyclin E to be recognized by Fbw7 (hCdc4) (Strohmaier, et al. (2001) supra), which is a phosphoepitope-specific substrate recognition component of SCF ubiquitin ligases.

During lung carcinogenesis, accumulation of genetic and epigenetic alterations causes invasive or metastatic lung cancers (Dragnev, et al. (2003) *Cancer Biol. Ther.* 2:S150-6). Lung cancer is the leading cause of cancer mortality for men and women in United States. Key molecular changes, especially at early stages of carcinogenesis, represent potential pharmacological targets for lung cancer chemoprevention and therapy. Aberrant expression of cyclin E has been frequently observed in premalignant lung lesions (Lonardo, et al. (1999) *Cancer Res.* 59:2470-6), indicating that this is an early step in lung carcinogenesis. Overexpression of cyclin E also occurs in overt non-small cell lung cancers (NSCLCs) and has prognostic significance in NSCLCs (Fukuse, et al. (2000) *Cancer Res.* 60:242-4; Muller-Tidow, et al. (2001) *Cancer Res.* 61:647-53; Dosaka-Akita, et al. (2001) *Cancer Res.* 61:2500-4). The mechanisms responsible for cyclin E deregulation in lung cancer are unknown. However, several mechanisms have been proposed in other tumor cells including gene amplification (Cassia, et al. (2003) *J. Pathol.* 201: 589-95; Schraml, et al. (2003) *J. Pathol.* 200:375-82), mutation in the F-box protein hCDC4 (Strohmaier, et al. (2001) supra; Spruck, et al. (2002) *Cancer Res.* 62:4535-9; Rajagopalan, et al. (2004) *Nature* 428:77-81), as well as proteolytic processing of full-length cyclin E at two sites in the amino-terminus by an elastase-like protease (Harwell, et al. (2000) *Cancer Res.* 60:481-9; Porter, et al. (2001) *Mol. Cell Biol.* 21:6254-69).

U.S. patent application Ser. No. 10/392,113 teaches a cell-based assay system comprising at least two manipulated (e.g., upregulated or down regulated) genes such as Cyclin E, Cyclin D, and the like, wherein the genes are involved in a disease state such as cancer for use in identifying a therapeutic reagent.

Retinoids, natural and synthetic derivatives of vitamin A, are active in cancer therapy and chemoprevention (Freemantle, et al. (2003) *Oncogene* 22:7305-15). The retinoid role in cancer chemoprevention has been highlighted by in vitro studies, preclinical animal model experiments, epidemiological evidence, and results of clinical trials wherein certain premalignant or second malignancies have been treated (Freemantle, et al. (2003) supra). All-trans-retinoic acid (RA) has been used as a pharmacologic tool to investigate RA chemopreventive mechanisms. A chemopreventive cell model has been established wherein immortalized BEAS-2B human bronchial epithelial cells are exposed to the carcinogen N-nitrosamine-4-(methylnitrosamino)-1-(3-pyridyl)-1-butanone (NNK) (Langenfeld, et al. (1996) *Oncogene* 13:1983-90). NNK-treated cells undergo cellular transformation resulting in increased proliferation, anchorage-independent growth, increased cyclin E expression and tumor formation in athymic mice (Langenfeld, et al. (1996) supra). RA antagonizes NNK-mediated transformation by causing G1 arrest (Langenfeld, et al. (1996) supra). This RA effect is associated with down-regulation of cyclin E and cyclin E-associated cdk2 kinase activity (Langenfeld, et al. (1996) supra). Further, RA represses cyclin E expression via activation of a proteosomal degradation pathway (Dragnev, et al. (2004) *Clin. Cancer Res.* 10:2570-7). These findings suggest proteolysis of cyclin E as an important cancer chemopreventive mechanism since the retinoid-induced G1 cell cycle arrest is expected to permit repair of carcinogenic damage to DNA. The critical role of cyclin E in RA response was confirmed in RA-resistant HBE cells with deregulated cyclin E expression (Dragnev, et al. (2004) supra).

The cyclin E mutant protein (cyclin E-Thr380Ala) stabilizes cyclin E and increases its associated kinase activity (Spruck, et al. (1999) supra). Moreover, overexpression of cyclin E (Thr380Ala) induces chromosome instability at a higher frequency than that observed in cells overexpressing wild-type cyclin E (Spruck, et al. (1999) supra). A cyclin E double mutant (Thr62Ala/Thr380Ala) is more stable than the Thr380Ala mutant (Nakayama, et al. (2000) *EMBO J.* 19:2069-81). Unlike wild-type cyclin E, which undergoes proteasome degradation, the cyclin E double-mutant protein (Thr62Ala/Thr380Ala) is stabilized after RA-treatment (Dragnev, et al. (2004) supra).

SUMMARY OF THE INVENTION

The present invention is a transgenic non-human animal whose genome contains a transgene composed of a nucleic acid encoding a cyclin E protein operably linked to a regulatory element composed of a lung-specific promoter so that cyclin E protein levels are elevated in the lung of the animal thereby promoting lung carcinogenesis. In one embodiment the animal is subject to a second stimulus which promotes lung carcinogenesis. In another embodiment, the cyclin E protein expressed by the animal is degradation resistant. A cell or cell line isolated from the transgenic non-human animal is also encompassed by the present invention.

The present invention is also a vector containing a transgene composed of a nucleic acid encoding a cyclin E protein operably linked to a regulatory element composed of a lung-specific promoter.

The present invention is further a method for identifying a therapeutic agent for the chemoprevention or treatment of lung cancer. In one embodiment, the method involves the steps of administering a test agent or combination of test agents to a transgenic non-human animal of the instant invention and determining whether the signs or symptoms associated with lung cancer are prevented, delayed or treated in the transgenic non-human animal thereby identifying a therapeutic agent for the chemoprevention or treatment of lung cancer. In another embodiment, the method involves the steps of contacting a cell or cell line isolated from a transgenic non-human animal of the instant invention with a test agent or combination of test agents and determining whether the expression or activity of cyclin E in the cell or cell line is inhibited or decreased thereby identifying a therapeutic agent for the chemoprevention or treatment of lung cancer.

BRIEF DESCRIPTION OF THE INVENTION

It has now been found that overexpression of cyclin E in lung epithelial cells promotes anchorage-independent cell growth, lung hyperplasia, lung adenocarcinoma and local metastasis. Because lung adenocarcinoma is a prevalent characteristic of human lung cancer, a transgenic animal overexpressing cyclin E in lung epithelial cells now provides a clinically relevant model system of human lung carcinogenesis.

Transgenic mice were exemplified herein to determine the role of cyclin E in lung carcinogenesis. Human cyclin E was constitutively overexpressed in transgenic mice under the control of the human surfactant C promoter (SP-C), which directs lung-specific gene expression. In addition to wild-type cyclin E, the stabilized mutant cyclin E (Thr62Ala/Thr380Ala) was independently used to generate transgenic mice to achieve expression of a degradation-resistant cyclin E. RNA interference techniques were used to investigate the functional role of E-type cyclin expression in regulating bronchial epithelial growth. Targeting each E-type cyclin inhibited human bronchial epithelial cell growth indicating that E-type cyclins are pharmacological targets for lung chemoprevention or therapy. Further, the classical and non-classical retinoids as well as the synthetic triterpinoid, 2-cyano-3,12-dioxooleana-1,9-dien-28-oic acid (CDDO), was found to potently repress exogenous cyclin E expression. Accordingly, the lung carcinogenesis animal model of the instant invention is useful for identifying and determining the efficacy of chemopreventive and chemotherapeutic agents in the chemoprevention and treatment of lung cancer.

To illustrate that cyclin E plays a role in oncogenic transformation, transduced mouse lung cell lines expressing cyclin D1 and cyclin E were generated. C10 immortalized mouse lung epithelial cells were independently infected with a retrovirus encoding cyclin D1-HA, myc-cyclin E or a corresponding empty control vector. Western blot analysis showed that exogenous cyclin D1 or cyclin E protein was highly expressed in cyclin D1 or cyclin E stably transduced cells, but not in the empty MSCV-neo or MSCV-hyg transduced cells. An anchorage-independent clonal growth assay revealed that cells overexpressing cyclin E displayed at least a three-fold increase in colony formation in soft agar as compared to empty MSCV-hyg transduced C10 cells. In contrast, overexpression of cyclin D1 had a minimal effect on anchorage-independent colony formation.

A genetic approach using siRNA was employed to target individual E-type cyclins (i.e., cyclin E and cyclin E2) to determine their functional roles in regulating human bronchial epithelial cell growth. Two independent siRNA molecules targeting different regions of each E-type cyclin were engineered; cyclin E-1 and cyclin E-2 targeting cyclin E, and cyclin E2-1 and cyclin E2-2 targeting cyclin E2.

Cyclin E-1 and cyclin E-2 siRNA treatment of BEAS-2B human bronchial epithelial cells repressed both cyclin E mRNA and protein expression. Twenty-four hours after transfection with cyclin E-1 or cyclin E-2 siRNAs, a respective 52% or 60% reduction in cyclin E mRNA was observed compared to cyclin E mRNA levels in cells transfected with control GL2 siRNA. Cyclin E2 expression was not affected in cells transfected with cyclin E siRNAs. Ninety-six hours after transfection with cyclin E-1 or cyclin E-2 siRNAs, a respective 75% or 37% reduction in cyclin E protein expression was observed, compared to cyclin E protein expression, in cells transfected with control GL2 siRNA. Further, repression of cyclin E by either cyclin E-1 or cyclin E-2 siRNA caused a statistically significant ($P<0.0001$) growth suppression of BEAS-2B cells.

Similarly, twenty-four hours after cyclin E2-1 or cyclin E2-2 siRNA transfection into BEAS-2B human bronchial epithelial cells, a respective 52% or 48% reduction in cyclin E2 mRNA expression was observed compared to cyclin E2 mRNA expression in cells transfected with GL2 siRNA. Cyclin E2 mRNA repression by these two independent siRNAs was still evident at 96 hours after transfection. Notably, cyclin E mRNA and protein expression were each enhanced by cyclin E2 siRNA treatment. The kinetics by which these independent cyclin E2 siRNAs induced cyclin E expression was different. Cyclin E2-1 siRNA displayed a more prominent effect on induction of cyclin E mRNA expression than did the cyclin E2-2 siRNA at 24 hours after transfection. Both cyclin E2 siRNAs significantly inhibited BEAS-2B cell growth.

Exogenous cyclin E expression promotes clonal growth of HBE cells (Langenfeld, et al. (1996) *Oncogene* 13:1983). C10 immortalized murine pulmonary epithelial cells were transduced with a retrovirus encoding wild-type or degradation-resistant human cyclin E or an insertless control vector. Transduction of a degradation-resistant cyclin E species (T62A/T380A) led to stabilization of this species as compared to the wild-type cyclin E species. In these immunoblot analyses, an anti-cyclin E antibody was used that identified the exogenous human, but not endogenous murine species. Wild-type cyclin E over-expressing C10 cells increased anchorage-independent colony formation as compared to controls. An even greater increase in anchorage-independent growth was observed after transduction of the degradation-resistant cyclin E species. These findings established a role for cyclin E in regulating growth of murine pulmonary epithelial cells. Stabilization of cyclin E was believed to augment tumorigenicity of cyclin E.

To determine whether other agents could modulate the expression of cyclin E, BEAS-2B cells were infected with a retrovirus encoding myc-cyclin B and treated with CDDO, N-(4-hydroxyphenyl)retinamide (4HPR or fenretinide), or other non-classical retinoids for 24, 36 and 48 hours. Among these agents, CDDO most potently decreased exogenous cyclin E expression, as early as 24 hours after treatment.

To demonstrate effects of exogenous cyclin E expression, independent murine transgenic lines were engineered to express wild-type or degradation-resistant human cyclin E (T62A/T380A) in the lung. These cyclin E transgenes were each driven by the human surfactant C promoter, which conferred expression in alveolar type II and brochioalveolar cells (Glasser, et al. (1991) *Am. J. Physiol* 261:L349-56). Two independent wild-type cyclin E and two independent degradation-resistant cyclin E (T62A/T380A) founder mice were identified by Southern blot analyses. Transgenic human cyclin E protein was detected using an immunoblot assay with an antibody, which recognized human, but not murine cyclin E protein in all transgenic lines, but not in nontransgenic (Tg-) control mice. The transgenic proteins migrated at 47 Kd and 37 Kd. This immunoblot expression profile was similar to that reported in the detection of cyclin E in T-lymphocytes (Karsunky, et al. (1999) *Oncogene* 18:7816). These two protein species were also present in the human lung cancer cell lines A549 and H520, and other lines.

Transgenic cyclin E protein expression levels were comparable in the wild-type cyclin E lines 1 and 2 and degradation-resistant cyclin E (T62A/T380A) line 4. Given this, findings from the wild-type cyclin E lines 1 and 2 were pooled. Degradation-resistant cyclin E transgenic line 3 had quite low expression levels of this transgenic protein. Immunohistochemical analyses revealed that human cyclin E expression was detected in the nuclei of bronchiolar epithelial cells and pneumocytes of wild-type cyclin E lines and the degradation-resistant cyclin E transgenic line 4, but was undetected in the Tg-mouse lung. The expected nuclear localization of exogenous human cyclin E protein was confirmed. Cyclin E immunostaining was detected in nuclei of some pneumocytes of the degradation-resistant transgenic cyclin E line 3. This independently established low levels of exogenous human cyclin E expression in this line.

Premalignancy and malignancy developed spontaneously in the lungs of wild-type and proteasome-degradation resistant cyclin E (T62A/T380A) transgenic mice. Histopathological analyses revealed alveolar dysplasia alone or with lung adenocarcinoma in these affected mice. The histopathological features of this pulmonary dysplasia were similar to that observed in clinical preneoplastic lesions (Lonardo, et al. (1999) *Cancer Res.* 59:2470). The lung adenocarcinomas in these transgenic mice had solid, papillary or mixed features that closely resembled features present in clinical lung cancer cases (Rusch, et al. (1997) *Clin. Cancer Res.* 3:515).

The incidences of dysplasia and lung cancer were each examined in wild-type and degradation-resistant cyclin E transgenic lines and compared to control Tg- mice. The onset of tumors was observed in some wild-type and degradation-resistant cyclin E transgenic lines occurring as early as 5 months of age. The majority of wild-type and degradation-resistant cyclin E transgenic mice were sacrificed at 10-14 months of age for analyses of pulmonary dysplasia and lung cancer incidence. Mice with advanced tumors exhibited symptoms of labored breathing and decreased body weight.

To confirm that onset of pulmonary dysplasia and tumor formation depended on transgenic cyclin E expression and not on the spontaneous lung tumor rate in the FVB/N murine line, cohorts of age-matched wild-type (Tg-) control mice were evaluated for pulmonary dysplasia and lung tumor formation. Among a total of 48 control mice, 4 had lung cancers and 2 more developed pulmonary dysplasia without evidence of pulmonary adenocarcinoma at 10-14 months of age. In marked contrast, 18 of 56 transgenic wild-type cyclin E lines 1 and 2 in this age range developed lung adenocarcinomas. Six of them developed both pulmonary dysplasia and adenocarcinoma and one mouse developed pulmonary dysplasia without lung adenocarcinoma. Seventeen of 34 degradation-resistant cyclin E transgenic line 4 mice developed lung adenocarcinomas and 8 of these mice developed both pulmonary dysplasia and adenocarcinoma. Three additional mice developed pulmonary dysplasia without lung adenocarcinoma. Seven of 42 degradation-resistant cyclin E transgenic line 3 mice developed lung adenocarcinomas. Two developed both pulmonary dysplasia and adenocarcinoma and another developed pulmonary dysplasia without a lung tumor. Wild-type cyclin E transgenic lines 1 and 2 had increased incidence of dysplasia as compared to control mice (13% versus 4%), but this difference was not statistically significant. Thirty-two % of wild-type cyclin E transgenic lines 1 and 2 and 8% of Tg-control mice developed lung tumors. The tumor incidence difference between these two groups was significant (P=0.001). The degradation-resistant cyclin E transgenic line 4 displayed a substantially higher incidence of dysplasia than control mice (32% versus 4%). This difference was significant (P=0.001).

Approximately half of degradation-resistant cyclin E transgenic line 4 mice developed lung cancers. The difference in cancer incidence between this transgenic line and control mice was significant (P<0.001). The degradation-resistant cyclin E line 3 had lower transgenic cyclin E expression in the lung as compared to line 4. The incidence in line 3 of dysplasia was higher than in control mice (10% versus 4%), but this difference was not statistically significant. Similar results were observed for incidence of lung tumors (17% versus 8%). Dysplasia and lung cancer incidences between degradation-resistant cyclin E lines were statistically different (P=0.013 and P<0.001, respectively). Thus, wild-type and degradation-resistant cyclin E transgenic expression both promoted dysplasia and lung tumor formation. The degradation-resistant cyclin E lines established a cyclin E protein dose-response relationship in lung carcinogenesis.

Pulmonary dysplasia and tumor formation incidences were compared for wild-type cyclin E transgenic lines 1 and 2 and for the degradation-resistant cyclin E transgenic line 4, which had comparable levels of exogenously expressed cyclin E proteins. Pulmonary dysplasia in degradation-resistant cyclin E transgenic line 4 was significantly higher than in wild-type cyclin E transgenic lines 1 and 2 (32% versus 13%, P=0.03). Lung cancers formed in degradation-resistant cyclin E transgenic line 4 more frequently than in wild-type cyclin E transgenic lines 1 and 2 (50% versus 32%), but this was not a statistically significant difference.

The incidence of multiple tumors in these transgenic lines was examined. All Tg-control mice that developed a lung cancer had a single tumor and 1.8% of wild-type cyclin E transgenic lines 1 and 2 mice and 2.4% of degradation-resistant cyclin E transgenic line 3 mice developed two lung cancers. Strikingly, 21% of degradation-resistant cyclin E transgenic line 4 mice developed at least two lung adenocarcinomas. The degradation-resistant cyclin E transgenic line 4 displayed a significant increase in incidence of multiple tumors relative to Tg-control mice, wild-type cyclin E transgenic lines (P=0.009) and degradation-resistant cyclin E transgenic line 3 (P=0.013). Thus, cyclin E stabilization by rendering this protein resistant to proteasomal degradation promoted onset of multiple lung cancers in transgenic mice.

Local metastases to the pleura and pulmonary lymph nodes were observed in some wild-type and degradation-resistant cyclin E transgenic mice. The presence of transgene-specific cyclin E protein in premalignant and malignant lesions from wild-type and degradation-resistant cyclin E transgenic mice strongly implicated cyclin E as an important regulator of murine lung carcinogenesis. Furthermore, the proliferation marker Ki-67 was more often immunohistohemically detected in dysplastic lesions and lung cancers of mice from wild-type and degradation-resistant cyclin E transgenic lines than in normal lungs of Tg-control mice. Dysplastic and malignant lung lesions caused by cyclin E over-expression were highly proliferative.

Cyclin E expression caused genomic instability as did cyclin E stabilization through a threonine to alanine transversion of residue 380 (T380A) (Spruck, et al. (1999) *Nature* 401:297. This resulted in increased associated kinase activity and chromosome instability (CIN) (Spruck, et al. (1999) supra). The degradation-resistant transgenic cyclin E protein species used herein is reported to be even more stable than cyclin E T380A (Strohmaier, et al. (2001) *Nature* 413:316). To address this association, CIN was examined in the lung cancers of wild-type and degradation-resistant cyclin E transgenic mice. CIN was measured by fluorescence in situ hybridization (FISH) using chromosome 4 and 6 markers. Aneuploidy of these chromosomes was frequently observed in murine lung adenocarcinoma cell lines (Sargent, et al. (2002) *Cancer Res.* 62:1152). The proportion of aneuploid tumor cells for each chromosome marker (chromosome gain) was higher in tumor cells expressing wild-type cyclin E or degradation-resistant transgenic cyclin E species than normal lung epithelial cells in Tg-control mice. This implicated CIN in these cyclin E transgenic mice as contributing to lung tumor formation.

Oncogenic events in addition to cyclin E over-expression likely contribute to murine lung carcinogenesis, as not all cyclin E transgenic mice developed pulmonary premalignancy or malignancy. Aberrant hedgehog (Hh) signaling is critical in the pathogenesis and maintenance of many cancers, including small cell lung cancers and non-small cell lung cancers (Pasca di Magliano &. Whether this pathway was activated in lung cancers derived from cyclin E transgenic mice was examined by independently probing immunoblots with anti-sonic hedgehog (Shh) and anti-Gli1 antibodies, respectively. Shh, a Hh pathway ligand (Pasca di Magliano & Hebrok (2003) supra), was over-expressed in 7 out of 8 examined lung cancers from wild-type cyclin E transgenic mice and 5 out of 6 examined lung tumors from degradation-resistant transgenic cyclin E mice as compared with the normal lung tissues in the same transgenic or control mice. Notably, Gli1, a transcriptional target of Hh signaling (Pasca di Magliano & Hebrok (2003) supra), was over-expressed in 4 of 8 examined lung cancers from wild-type transgenic cyclin E mice and 4 of 6 lung cancers from degradation-resistant transgenic cyclin E mice as compared with the normal lung tissues from the same transgenic mice. As additional controls, normal lungs from age- and sex-matched non-transgenic control mice, wild-type transgenic cyclin E and degradation-resistant cyclin E transgenic mice without evidence of lung adenocarcinomas were examined and found to have low or undetected Shh and Gli protein expression.

Gli1 and Shh expression profiles were frequently found to overlap. Among 5 examined tumors from degradation-resistant cyclin E transgenic mice, 4 had both Gli1 and Shh over-expression; one displayed only Shh over-expression. These findings were confirmed by an immunohistochemical assay. Gli1 expression was activated in dysplastic and malignant lung lesions from transgenic cyclin E mice. This frequent activation of the Shh pathway in lung adenocarcinomas from cyclin E transgenic mice argues against this as a random event.

Whether over-expression of wild-type or degradation-resistant cyclin E activated the Shh pathway in C10 cells was examined. Reverse transcription-polymerase chain reaction (RT-PCR) assays were used to assess mRNA expression of Shh pathway components, including smoothened (Smo), Gli1 and Patched (Ptc) in C10 cells transduced with wild-type or degradation-resistant human cyclin E. Findings were compared to those in insertless vector transduced C10 cells. An increase in mRNA expression for Smo, Gli1, and Ptc was observed following exogenous cyclin E expression. Smo, a transmembrane protein, activates the Hh pathway by affecting the transcription factor Gli1. Ptc, a transmembrane receptor, when bound to Hh ligands, can block Smo function. Both Ptc and Gli1 are transcriptional targets of Hh signaling. mRNA expression profiles of Smo, Gli1 and Ptc increased in C10 cells over-expressing wild-type or degradation-resistant human cyclin E as compared to control cells. Shh mRNA expression was unable to be detected, indicating the relatively low abundance of this species in mouse lung epithelial cells. These findings indicate the Hh pathway is activated by cyclin E. This might serve a reciprocal functional role as Hh signaling is known to activate cyclin E expression (Duman-Scheel, et al. (2002) *Nature* 417:299). CIN from cyclin E over-expression likely contributes to these and other oncogenic events.

The findings disclosed herein indicate a direct role for cyclin E in murine lung carcinogenesis. Cyclin E transgenic lines reproduce frequent features of human lung carcinogenesis, including onset of dysplasia, single or multiple lung adenocarcinomas, and activation of the Hh pathway (Pasca di Magliano & Hebrok (2003) supra; Watkins, et al. (2003) supra; Robbins, et al. (2005) *Current Cancer Therapy Reviews* 1:227). That forced over-expression of cyclin E results in lung carcinogenesis reminiscent of the human disease highlights cyclin E as a critical target for lung cancer therapy or chemoprevention.

Having demonstrated that overexpression of cyclin E promotes lung carcinogenesis, the present invention is a transgenic non-human animal overexpressing cyclin E in a lung-specific manner for use in studying the etiology of lung cancer and the identification of chemopreventive and therapeutic agents for the chemoprevention and treatment of lung premalignancies and overt NSCLCs. The transgenic non-human animal of the instant invention is produced by introducing into an animal host an expression vector harboring a cyclin E nucleic acid operably linked to a regulatory element which specifically directs expression of cyclin E in the lung of the animal so that lung carcinogenesis is promoted. As used herein, promotion of lung carcinogenesis is intended to include the development of tumors (i.e., tumorigenesis), as well as abnormalities such as hyperplastic lesions, in an animal which otherwise would not readily develop signs of lung carcinogenesis.

A cyclin E nucleic acid or nucleic acid encoding cyclin E generally refers to nucleic acid molecules encoding cyclin E (also referred to as cyclin E1) or cyclin E2. Cyclin E nucleic acid molecules can encode for a full-length cyclin E or low molecular weight isoforms of cyclin E, which have been found to give tumor cells a growth advantage by increasing the affinity for cdk2 and resistance to inhibition by the cyclin-dependent kinase inhibitors p21 and p27, increasing resistance to the growth inhibiting effects of antiestrogens, and increasing chromosomal instability (Akli, et al. (2004) *Cancer Res.* 64(9):3198-208). Nucleic acid molecules encoding cyclin E are well-known in the art and include, but are not limited to, GENBANK Accession Nos. NM_001238 and NM_057182, which encode human cyclin E (Koff, et al. (1991) *Cell* 66:1217-1228; Sewing, et al. (1994) *J. Cell. Sci.* 107:581-588), and GENBANK Accession Nos. NM_004702, NM_057735, and NM_057749, which encode human cyclin E2 (Lauper, et al. (1998) *Oncogene* 17:2637-2643; Gudas, et al. (1999) *Mol. Cell. Biol.* 19:612-

622). Other suitable cyclin E nucleic acid molecules can be identified by routine stringent hybridization (e.g., hybridization conditions of 60° C. in 2×SSC buffer) or sequence analysis (e.g., BLAST sequence analysis), using well-established methods. See, e.g., Sambrook, et al. (1989) Molecular Cloning: A Laboratory Manual, Second Edition, Cold Spring Harbor Laboratory Press, Cold Spring Harbor, N.Y. In one embodiment, the cyclin E is a heterologous cyclin E, i.e., derived from a source other than the host animal being transformed. In another embodiment, the cyclin E is of human origin. In particular embodiments, the cyclin E nucleic acid of the instant transgenic animal encodes a human cyclin E1 protein, e.g., GENBANK Accession No. NM_001238 or NM_057182; or SEQ ID NO:1.

A cyclin E nucleic acid of the instant invention also encompasses cyclin E nucleic acids which encode degradation-resistant forms of cyclin E. Degradation-resistant forms of cyclin E are well-known in the art. See, e.g., Dragnev, et al. (2004) supra. Particularly suitable degradation-resistant forms of cyclin E include cyclin E Thr62Ala, cyclin E Thr380Ala, or a combination thereof, i.e., a cyclin E Thr62Ala/Thr380Ala double mutant.

The instant invention further embraces chimeric cyclin E nucleic acid molecules. For example, a cyclin E nucleic acid molecule can be fused or operably linked to a second (or more) nucleic acid molecule encoding a second protein such that a chimeric nucleic acid molecule is produced. The chimeric nucleic acid molecule can encode a fusion protein in which the two (or more) encoded proteins are translated in-frame to form a single protein, i.e., they are covalently bound through a peptide bond; or the chimeric nucleic acid molecule can be translated into two discrete proteins, e.g., a bicistronic message with an internal ribosome entry site (IRES) located between the coding regions for cyclin E and the second protein. A chimeric cyclin E nucleic acid molecule can encode, for example, cyclin E and a reporter molecule (e.g., green fluorescent protein (GFP), enhanced GFP, luciferase, beta-glucuronidase, etc.) or a peptide tag (e.g., His-6, c-myc, FLAG® epitope, biotin, or the like) to facilitate the monitoring of cyclin E expression. When the chimeric cyclin E nucleic acid encodes a fusion protein, desirably the fusion protein demonstrates some or all of the characteristics of each of its protein components. As such, a fusion between cyclin E and, e.g., GFP, retains the ability to promote lung carcinogenesis and is concurrently fluorescent.

The term nucleic acid molecules includes RNA and DNA, which can be a gene or a portion thereof, a cDNA, a synthetic polydeoxyribonucleic acid sequence, or the like, and can be single-stranded or double-stranded, as well as a DNA/RNA hybrid. Furthermore, the term nucleic acid, as used herein, includes naturally occurring nucleic acid molecules, which can be isolated from a cell, as well as synthetic molecules, which can be prepared, for example, by methods of chemical synthesis or by enzymatic methods such as by the polymerase chain reaction (PCR) using an appropriate template.

To achieve lung-specific expression in the transgenic animal, the cyclin E nucleic acid is operably linked to a regulatory element containing a lung-specific promoter. As used herein, operably linked or operably associated means that two or more molecules are positioned with respect to each other such that they act as a single unit and effect a function attributable to one or both molecules or a combination thereof. For example, a nucleic acid molecule encoding a cyclin E protein of the invention can be operably linked to a regulatory element, in which case the regulatory element confers its regulatory effect on the cyclin E nucleic acid similar to the way in which the regulatory element would effect a nucleic acid molecule with which it normally is associated within a cell. Alternatively stated, a regulatory element containing a lung-specific promoter, which is operably linked to a cyclin E nucleic acid, will direct lung-specific transcription of a cyclin E mRNA and subsequent translation of a cyclin E protein.

A regulatory element of the instant invention encompasses a lung-specific promoter, which provides constitutive or, if desired, inducible lung tissue-specific transcription of cyclin E mRNA; a ribosome recognition site or internal ribosome entry site; or other control sequences such as enhancers or introns. As used herein, a lung-specific promoter controls transcription of cyclin E mRNA, such that overexpression of cyclin E protein is restricted to the lung cells in an animal, or to lungs cells in a mixed population of cells in culture, for example, an organ culture. Lung cell-specific promoters including, for example, human surfactant C protein (Duan et al. (2002) *Oncogene* 21:7831-8; Ehrhardt, et al. (2001) Br. J. Cancer 84(6):813-818), Clara cell secretory protein (CCSP) promoter (Graham, et al. (2001) *Am. J. Respir. Crit. Care Med.* 164(2):307-313), Jaagskiekte sheep retrovirus (JSRV) long-terminal repeat (Palmarini, et al. (2000) *J. Virol.* 74(13): 5776-5787), rat aquaporin-5 promoter (Borok, et al. (2000) J. Biol. Chem. 275(34):26507-26514) and other human surfactant A1, A2, B, or D protein promoters are well-known in the art. Still other lung-specific promoters can be readily selected by one of skill in the art for use in the invention. The lung-specific promoter can be species-heterologous with respect to the cyclin E nucleic acid, i.e., from a species which is different from the origin of the cyclin E nucleic acid. Alternatively, the lung-specific promoter can be species-homologous with respect to the cyclin E nucleic acid, i.e., from the same species from which the cyclin E nucleic acid was isolated. Whether species-heterologous or species-homologous, the lung-specific promoter should direct tissue-specific overexpression of cyclin E in the transgenic animal. Lung-specific overexpression of cyclin E can be confirmed by immunocytochemical analysis or reporter protein expression, in the case of a cyclin E/reporter fusion protein. In particular embodiments, lung-specific overexpression of cyclin E results in elevated levels of cyclin E protein in lung cells (e.g., alveolar cells) of the transgenic compared to cyclin E protein levels a non-transgenic control animal. As exemplified herein, elevated cyclin E protein levels increase the occurrence of lung hyperplasia and tumors in transgenic animals (i.e., increase lung carcinogenesis), where spontaneous tumor development was not observed in non-transgenic animals of the same strain. Moreover, lung tumor development in these animals correlated with the expression level of transgenic cyclin E protein; the cyclin E transgenic line with higher cyclin E expression exhibited an earlier onset of tumor development, larger tumor size and more advanced pathologic changes than that of a transgenic line with lower cyclin E expression.

The transgene of the instant invention, i.e., a nucleic acid encoding a cyclin E protein operably linked to a regulatory element, can be stably inserted into cells within the transgenic animal as naked DNA or more commonly as part of a vector to facilitate manipulation of the transgene. As used herein, the term transgene refers to a nucleic acid molecule (e.g., encoding one or more proteins), which is inserted by artifice into a cell and is stably integrated into the chromosomal genome of the cell or is stably maintained as an episome. In embodiments of the invention, the transgene is integrated into the chromosomal genome resulting in a transgenic animal. It is not necessary that every cell of the transgenic animal contain the transgene, and the animal can be a chimera of modified and unmodified cells, as long as a sufficient number of cells contain and overexpress the cyclin E protein in lung epithelial cells.

A vector of the instant invention generally contains, in addition to the transgene, elements required for replication in a prokaryotic or eukaryotic host system or both, as desired. Such vectors, which include plasmid vectors and viral vectors are well-known and can be purchased from a commercial source (PROMEGA®, Madison, Wis.; STRATAGENE®, La Jolla, Calif.; GIBCO/BRL®, Gaithersburg, Md.) or can be constructed by one skilled in the art (see, for example, Goeddel (1990) *Meth. Enzymol.* Vol. 185, Academic Press, Inc.; Jolly (1994) *Canc. Gene Ther.* 1:51-64; Flotte (1993) *Bioenerg. Biomemb.* 25:37-42; Kirshenbaum, et al. (1993) *J. Clin. Invest.* 92:381-387).

Viral expression vectors can be particularly useful for introducing a transgene into a cell, particularly a cell in an animal. Viral vectors provide the advantage that they can infect host cells with relatively high efficiency and can infect specific cell types. The viral vector also can be derived from a virus that infects cells of an animal of interest, for example, vertebrate host cells such as chimpanzee host cells. Viral vectors have been developed for use in particular mammalian systems and include, for example, retroviral vectors, other lentivirus vectors such as those based on the human immunodeficiency virus (HIV), semliki forest virus, adenovirus vectors, adeno-associated virus vectors, herpesvirus vectors, vaccinia virus vectors, and the like (see Miller and Rosman (1992) *BioTechniques* 7:980-990; Anderson, et al. (1998) *Nature* 392:25-30; Verma and Somia (1997) *Nature* 389:239-242; and Wilson (1996) *New Engl. J. Med.* 334:1185-1187 (1996).

When retroviruses, for example, are used for gene transfer, replication-competent retroviruses theoretically can develop due to recombination of retroviral vector and viral gene sequences in the packaging cell line utilized to produce the retroviral vector. Packaging cell lines in which the production of replication competent virus by recombination has been reduced or eliminated can be used to minimize the likelihood that a replication competent retrovirus will be produced. All retroviral vector supernatants used to infect cells are screened for replication competent virus by standard assays such as PCR and reverse transcriptase assays. Retroviral vectors allow for integration of a heterologous transgene into a host cell genome, which allows for the gene to be passed to daughter cells following cell division.

Introduction of a transgene into a cell by infection with a viral vector is particularly advantageous in that it can efficiently introduce the nucleic acid molecule into a cell ex vivo or in vivo (see, for example, U.S. Pat. No. 5,399,346). Moreover, viruses are very specialized and can be selected as vectors based on an ability to infect and propagate in one or a few specific cell types. Thus, their natural specificity can be used to target the transgene contained in the vector to specific cell types. As such, a vector based on an adenovirus can be used, for example, to infect respiratory epithelial cells. Other vectors, such as adeno-associated viruses can have greater host cell range and, therefore, can be used to infect various cell types, although viral or non-viral vectors also can be modified with specific receptors or ligands to alter target specificity through receptor-mediated events.

As an alternative to viral vector infection, a variety of other methods are well-known in the art for introducing a transgene or vector into a host cell or animal (Sambrook, et al. (1989) supra; Ausubel, et al. (1995) Current Protocols in Molecular Biology, John Wiley and Sons, Baltimore, Md., and other laboratory manuals). Such methods include, for example, transfection, lipofection, microinjection, and electroporation; and can include the use of liposomes, microemulsions or the like, which can facilitate introduction of the transgene into the cell and can protect the transgene from degradation prior to its introduction into the cell. The selection of a particular method will depend, for example, on the cell into which the transgene is to be introduced, as well as whether the cell is isolated in culture, or is in a tissue or organ in culture or in situ.

In one method, an embryo is harvested from a female and the transgene is introduced into embryonal target cells at various developmental stages, wherein different methods are selected depending on the stage of development of the embryonal target cell. For example, the zygote is the best target for microinjection. The use of zygotes as a target for gene transfer has a major advantage in that the injected DNA can incorporate into the host genome before the first cell division (Brinster, et al. (1985) *Proc. Natl. Acad. Sci. USA* 82:4438-4442). Consequently, all cells of the transgenic non-human animal carry one or more copies of the incorporated transgene, thus contributing to efficient transmission of the transgene to offspring of the founder, since 50% of the germ cells will harbor the transgene. Following introduction of the transgene into the embryo, the embryo can be incubated in vitro for varying amounts of time, or reimplanted into the surrogate host, or both. One common method is to incubate the embryos in vitro for about 1-7 days, depending on the species, and then reimplant them into the surrogate host.

In another method, embryonic stem cells or somatic cells (e.g., fibroblasts) are isolated and the transgene is incorporated into the cells by electroporation, plasmid transfection, retroviral infection, or microinjection. Such transformed cells can thereafter be combined with blastocysts or enucleated oocytes from a non-human animal (Evans, et al. (1981) *Nature* 292:154-156; Bradley, et al. (1984) *Nature* 309:255-258; Gossler, et al. (1986) *Proc. Natl. Acad. Sci. USA* 83:9065-9069; Robertson, et al. (1986) *Nature* 322:445-448). The cells thereafter contribute to the germ line of the resulting animal (see Jaenisch (1988) *Science* 240:1468-1474). A particularly suitable method for producing a transgenic non-human animal of the instant invention is disclosed in U.S. Pat. No. 6,580,017 which teaches a method for producing and maintaining a reconstructed embryo in culture, transferring the embryo into a recipient mammal, and allowing the embryo to develop into a mammal.

The progeny of the transgenic embryos can be tested for the presence of the construct (e.g., by Southern blot analysis) of a segment of tissue. An embryo having one or more copies of the transgene stably integrated into the genome can be used to establish a permanent transgenic animal line carrying the transgene.

Transgenically altered animals can be assayed after birth for the incorporation of the transgene into the genome of the offspring. This can be done by hybridizing a probe corresponding to the DNA sequence coding for cyclin E or a segment thereof onto chromosomal material from the progeny. Those progeny found to contain at least one copy of the transgene in their genome are grown to maturity. In particular embodiments, the transgenic animal has more than one copy of the transgene in its genome.

Using methods such as those disclosed herein, various transgenic non-human animals have been routinely produced. For example, McCreath et al. ((2000) *Nature* 405:1066-1069) disclose efficient and reproducible gene expression of human α1-antitrypsin at the ovine α1(I) procollagen locus by employing transformed fetal fibroblasts. Moreover, Lai et al. (2002) *Science* 295:1089-92) teach transformation of clonal fetal fibroblast cell lines and the use thereof as nuclear donors for embryos reconstructed with enucleated pig oocytes. Accordingly, while mice are exemplified herein, other suitable animal hosts include rats, monkeys, dogs, rabbits, guinea pigs, goats, sheep, pigs and cattle. In one embodiment the transgenic non-human animal of the instant invention is a rodent. In particular embodiments, the transgenic non-human animal of the instant invention is a mouse.

Transgenic animals of the present invention exhibit a high rate of lung carcinogenesis. Transgenic animals of the invention can be produced in a short period of time and identified by the presence of lung abnormalities including respiratory epithelial premalignancies (hyperplasia, dysplasia and atypia) and adenocarcinoma with papillary or occasionally BAC features associated with lung. Animals exhibiting such lung abnormalities are useful as models to study possible therapies including pharmaceutical intervention, gene targeting techniques, antisense therapies, antibody therapies, etc. Furthermore, such animals can be used to examine the genomic instability that occurs from transgenic cyclin E expression which sets the stage for secondary genetic alteration that promote lung carcinogenesis. Moreover, the instant animals can be used to analyze situations or environmental hazards or carcinogenic exposures which are suspected of accelerating or initiating lung cancer, such as for example, exposure to airborne pollutants or infection. Thus, in accordance with one embodiment of the instant invention, a transgenic animal expressing elevated levels of cyclin E protein in the lung is subjected or exposed to a second stimulus which promotes lung carcinogenesis. As used herein, the second stimulus can be an environmental pollutant (e.g., asbestos) or other known lung carcinogen (e.g., second-hand smoke). The second stimulus can also encompass mating the transgenic animal of the instant invention with another animal model of lung carcinogenesis. Suitable mating partners include, but are not limited to, mice overexpressing SV40 T antigen or p53-273H, mice with conditional inactivation of p53, or mice with conditional knock-in K-rasG12D (Wikenheiser, et al. (1992) *Cancer Res.* 52:5342-52; Duan, et al. (2002) *Oncogene* 21:7831-8; Jackson, et al. (2001) *Genes Dev.* 15:3243-8; Meuwissen, et al. (2001) *Oncogene* 20:6551-8; Meuwissen, et al. (2003) *Cancer Cell.* 4:181-9). Desirably, the second stimulus decreases tumor latency or increases tumor incidence in the transgenic animal expressing elevated levels of cyclin E protein in the lung thereby providing alternative models of lung carcinogenesis.

The transgenic non-human animal, or cells or cell lines isolated from said transgenic non-human animal, are useful for the discovery and development of chemopreventive agents and therapeutic agents for the prevention and treatment of lung cancer including premalignant lung lesions and overt non-small cell lung cancers. Accordingly, the present invention is also a method for identifying or screening for chemopreventive or therapeutic agents which prevent (i.e., inhibit or delay the development or onset of) or treat lung cancer. In one embodiment, the screening method involves administering a test agent or a combination of test agents to a transgenic animal of the instant invention either prior to or after onset of tumor formation and determining whether the signs or symptoms associated with lung cancer are prevented, delayed, or treated as compared to a control animal. A control animal can include a non-transgenic animal which has not been administered a test agent, a sham-treated transgenic animal, or a combination of both can be used for comparison. In cases where the test agent(s) is administered prior to onset of tumorigenesis, the transgenic animal is monitored for the prevention or delay of onset of signs or symptoms such as premalignant hyperplasia or adenocarcinoma formation as well as Gli1 and Shh over-expression. In cases where the test agent is administered after signs or symptoms of lung tumorigenesis have been detected (e.g., a tumor or hyperplasia), the animal is monitored for the delay of onset of advanced signs or symptoms (e.g., tumor metastasis) or treatment of signs or symptoms (e.g., a reduction in tumor size). Signs or symptoms of lung tumorigenesis can be monitored by examining the animal's vital signs or by biopsy or determining the expression level of Gli1 and Shh.

In another embodiment, the screening method involves contacting a cell or cell line isolated from a transgenic animal of the instant invention with a test agent or combination of test agents and determining whether the agent inhibits or decreases (e.g., by 10%, 20%, 30%, 40%, 50%, 60%, 70%, 80%, 90%, or 95%) the expression or activity of cyclin E, Gli1 or Shh as compared to a control cell or cell line which has not been contacted with the test agent. In one embodiment, the cell or cell line employed is isolated from a tumor of the transgenic animal. In another embodiment, the cell or cell line is isolated from lung tissue which does not exhibit any signs or symptoms of lung cancer. One of skill in the art will appreciate that any well-established method can be employed for determining whether the agent decreases the expression or activity of cyclin E, Gli1 or Shh. For example, standard northern blot or RT-PCR analyses can be used to monitor mRNA levels. Optionally, protein levels can be determined by western blot analysis or measuring fluorescence of a reporter protein fused to cyclin E, Gli1 or Shh promoter.

Test agents which can be screened in accordance with the screening assays provided herein encompass numerous chemical classes, though typically they are organic molecules, preferably small organic compounds having a molecular weight of more than 100 and less than about 2,500 daltons. Libraries of such compounds can contain either collections of pure agents or collections of agent mixtures. Examples of pure agents include, but are not limited to, proteins, antibodies, peptides, peptide aptamers, nucleic acids, oligonucleotides, carbohydrates, lipids, synthetic or semi-synthetic chemicals, and purified natural products. Such libraries are commercially available to the skilled artisan. Examples of agent mixtures include, but are not limited to, extracts of prokaryotic or eukaryotic cells and tissues, as well as fermentation broths and cell or tissue culture supernates. In particular embodiments, agents identified in accordance with the screening methods of the instant invention decrease the amount or activity of cyclin E, Gli1 or Shh (e.g., increase degradation or expression) or affect the activity of proteins which interact with cyclin E. Exemplary agents include CDDO and the siRNA molecules disclosed herein. Other suitable agents which can be screened are inhibitors of the Shh pathway.

Agents identified by the methods disclosed herein can be formulated with appropriate carriers or diluents, which further can be pharmaceutically acceptable. The means of making such a pharmaceutical composition have been described in the art (see, for instance, Remington's Pharmaceutical Sciences, 16th Ed., Mack, ed. (1980)). Certain pharmaceutical compositions are single unit dosage forms suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to, tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration requires enteric coatings to protect the agents of the invention from degradation within the gastrointestinal tract. In another example, the agents of the invention may be administered in a liposomal formulation to shield the agents from degradative enzymes, facilitate transport in circulatory system, and effect delivery across cell membranes to intracellular sites.

The composition, shape, and type of dosage forms of the invention will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by the invention will vary from one another and will be readily apparent to those skilled in the art.

The following non-limiting examples are provided to further illustrate the present invention.

EXAMPLE 1

Cell Culture and Recombinant Plasmids

BEAS-2B cells, SV40 large T antigen immortalized human bronchial epithelial (HBE) cells, were cultured in serum-free LHC-9 media (Biofluids, Rockville, Md.) according to established methods (Ma, et al. (2005) *Cancer Res.* 65:6476). The C10 cell line is a non-tumorigenic murine alveolar type II epithelial cell line and was cloned from the NAL 1A alveolar type II epithelial cell line (Malkinson et al. (1997) *Toxicology* 123:53). C10 cells were cultured in CMRL 1066 medium (Life Technologies, Grand Island, N.Y.) supplemented with 10% fetal bovine serum (FBS), 2 mM L-glutamine and 100 IU/ml penicillin and 100 µg/ml streptomycin. GP2-293, a GP293-based packaging cell line that stably expressed the gag and pol genes of vesicular stomatitis virus (VSV) was purchased (BD Bioscience Clontech, Palo Alto, Calif.). This line was maintained in DMEM (BD Bioscience Clontech, Palo Alto, Calif.) supplemented with 10% FBS, 4 mM L-glutamate, 1 mM sodium pyruvate and supplemented with 100 IU/ml penicillin and 100 µg/ml streptomycin. All the cell lines were cultured at 37° C. in a humidified incubator with 5% $CO_2$. The pVSV-G vector that expressed the envelope glycoprotein of VSV from the cytomegalovirus promoter was also purchased (BD Bioscience Clontech, Palo Alto, Calif.). Full-length cDNAs for myc-tagged human wild-type cyclin E and T62A/T380A cyclin E were independently engineered by DraI/EcoRV restriction endonuclease digestion of CS2-myc-wild-type cyclin E and CS2-myc-T62A/T380A cyclin E plasmids (Dragnev, et al. (2004) *Clin. Cancer Res.* 10:2670) and ligated into a unique HpaI restriction endonuclease site of the pMSCVhyg retroviral expression vector (BD Bioscience Clontech, Palo Alto, Calif.) that contains the hygromycin resistance gene.

EXAMPLE 2

Plasmid Transfection and Retrovirus Infection

The pMSCVhyg, pMSCVhyg-myc-cyclin E and pMSCVhyg-myc-T62A/T380A cyclin E vectors were independently cotransfected with the PVSV-G plasmid into GP2-293 cells using the LIPOFECTAMINE 2000 reagent (INVITROGEN, Carlsbad, Calif.) and techniques established by the manufacturer. C10 cells were independently transduced with each recombinant retrovirus. Two days after transfection, media were used for viral transduction of C10 cells in the presence of 8 µg/ml POLYBRENE (Sigma, St. Louis, Mo.). After 24 hours, cells were cultured in fresh media, and 48 hours after transduction, cells were selected with hygromycin B (250 µg/ml) (Sigma, St. Louis, Mo.) for two weeks to obtain stable transductants.

EXAMPLE 3 siRNA Experiments

Double-stranded siRNAs with a 21-nucleotide duplex RNA and a 2-nucleotide overhang at the 3' region were each synthesized (QIAGEN, Valencia, Calif.). The siRNAs was designed to target human cyclin E coding regions. Cyclin E mRNA target sequence was 5'-AAG TGC TAC TGC CGC AGT ATC-3' (SEQ ID NO:2). Firefly luciferase GL2 siRNA (Dharmacon, Lafayette, Colo.) served as an siRNA duplex control. Transfection of siRNA was accomplished using established methods (Ma, et al. (2005) *Cancer Res.* 65:6476). To assess effects of transfection on cell growth, $2.5\times10^4$ viable BEAS-2B HBE cells were plated onto 12-well plates 24 hours after siRNA transfection. Viable cells were determined by a modified 3-(4,5-dimethylthiazol-2yl)-2,5-diphenyl tetrazolium bromide (MTT) colorimetric assay (Nason-Burchenal, et al. (1998) *Blood* 92:1758). Briefly, MTT was added to each well so that the final concentration of MTT was 1 mg/ml. This mixture was incubated for 4 hours at 37° C. and assays were performed. At the end of the incubation period, medium was removed and 1 ml of isopropanol was added onto each plate. Plates were assayed using a Molecular Devices microplate reader (Sunnyvale, Calif.) at a wavelength of 570 nm. Three independent triplicate experiments were performed. The second cyclin E siRNA targeting a different cyclin E coding region (5'-CAG TGG TGC GAC ATA GAG AAC-3'; SEQ ID NO:3) was also engineered and used to independently confirm the results.

EXAMPLE 4

Anchorage Independent Clonal Growth Assay

Soft agar anchorage independent clonal growth assays were performed using established techniques (Dmitrovsky, et al. (1990) *Oncogene Res.* 5:233). $5\times10^4$ C10 cells were plated onto each 6 well tissue culture plate and cultured in soft agar containing 20% FBS. Two weeks after plating, colonies 75 µm in size or larger were counted. Medium was changed once every week. Three independent triplicate experiments were performed and results pooled for analyses.

EXAMPLE 5

Engineering Cyclin E Transgenic Lines

The human surfactant C (SP-C) driven wild-type and degradation-resistant cyclin E (T62A/T380A) cDNAs were each engineered by independent restriction endonuclease digestions of CS2-wild-type and degradation-resistant cyclin E containing plasmids (Dragnev, et al. (2004) *Toxicology* 123:53) using EcoRI and HindIII restriction endonucleases. These derived cDNAs were subsequently inserted into the SP-C-3.7-SV40 plasmid, which was linearized by EcoRI and HindIII partial restriction endonuclease digestions. For microinjection, the SP-C/wild-type cyclin E and SP-C/degradation-resistant cyclin E (T62A/T380A) constructs were each isolated by NedI/NotI restriction endonuclease digestions, and the desired 5.6 Kb transgenic inserts were purified by size-fractionation using agarose gel electrophoresis. Transgenic murine lines were independently generated by injection of these recombinant DNA fragments into fertilized eggs of FVB/N mice (Bar Harbor, Me.) using established techniques (Early, et al. (1996) *Proc. Natl. Acad. Sci. USA* 93:7900). Mice were analyzed for transgenic integration by Southern analyses (Bender, et al. (2000) *Blood* 95:3600) of genomic DNA harvested from tails of individual mice using the DNEASY Tissue kit (QIAGEN, Valencia). Tail DNA was digested with BamHI restriction endonuclease. The probe for Southern blot analysis was a $P^{32}$-labeled 0.4 Kb SV40 T-intron-poly (A) DNA fragment derived from the SP-C-3.7-SV40 plasmid. Mice of subsequent generations were screened for the presence of the transgene by use of a polymerase chain reaction (PCR) method (Ma, et al. (2005) *Cancer Res.* 65:6476). The transgene-specific PCR products included the SP-C promoter region and the respective cyclin E cDNA coding domain. The primers for PCR were for the forward primer: 5'-TTA TCT GGG CTT CGG TTC TG-3' (SEQ ID NO:4) and for the reverse primer: 5'-TCG ATT TTG GCC ATT TCT TC-3' (SEQ ID NO:5).

EXAMPLE 6

Histopathology and Immunohistochemistry

Lung tissues obtained from control and transgenic mice were fixed in 10% neutral buffered formalin, embedded in paraffin, cut in 5 micron thick sections, heated and then deparaffinized with xylene. The tissue was rehydrated with serial dilutions of ethanol. Antigen retrieval was performed in a pressure cooker for 40 minutes total at a maximum of 19 PSI and 127° C. using a citrate buffer (Biogenex, San Ramos, Calif.) Peroxide was then blocked with a 3% solution of hydrogen peroxide. Buffered casein solution was used as a non-specific blocking agent. The tissue was incubated with 1:50 dilution of murine monoclonal anti-cyclin E antibodies that specifically recognized human cyclin E protein (HE 12; Neomarkers, Fremont, Calif.) for 30 minutes; or a 1:400 dilution of a rabbit monoclonal anti-Ki67 antibody (Vector Laboratories, Burlingame, Calif.) for 30 minutes, or a 1:200 dilution of rabbit polyclonal anti-Gli1 antibody (Abcam, Cambridge, Mass.) for 30 minutes. Primary antibody was detected with a peroxidase-conjugated streptavidin method with the dimethylbenzadene substrate chromagen (Biogenex, San Ramon, Calif.), and a light hematoxylin counterstain. The tissue was then dehydrated with serial ethanol solutions and finally with xylene. The controls stained appropriately. Immunostaining and routine histology analyses of these lung tissues were conducted by a pathologist who was blinded as to the information of whether the murine line was transgenic or not.

EXAMPLE 7

Immunoblot Analyses

Protein extracts were isolated from harvested and snap-frozen murine lung tissues and by homogenization or from cells by lysis in radioimmunoprecipitation assay (RIPA) lysis buffer, as described previously (Ma, et al. (2005) supra). These extracts were centrifuged at 10,000 g to remove the tissue debris. Protein concentrations were determined using Bradford assays (BIO-RAD, Hercules, Calif.). Western blot analyses were performed using established methods (Ma, et al. (2005) supra). Primary antibodies used included murine monoclonal antibodies that recognized human cyclin E (HE-12, Santa Cruz Biotechnology, Santa Cruz, Calif.), a goat polyclonal antibody that recognized actin (C11, Santa Cruz Biotechnology, Santa Cruz, Calif.), and rabbit polyclonal antibodies that independently recognized sonic hedgehog (Shh) (H-160, Santa Cruz Biotechnology, Santa Cruz, Calif.) or Gli1 (Abcam, Cambridge, Mass.). Antimurine antisera and anti-rabbit antisera were purchased (Amersham Biosciences, Piscataway, N.J.) as was the anti-goat antisera (Santa Cruz Biotechnology, Santa Cruz, Calif.).

EXAMPLE 8

Statistical Analyses

Values from siRNA experiments and anchorage-independent clonal growth assays were expressed as mean±standard deviation (SD). Incidence of lung dysplasia and cancers were expressed as mean±standard error (SE). A two-sided test was used on proportion for group comparison, (Rice (1995) *Mathematical Statistics and Data Analysis* (Duxbury Press, Belmont, Calif., ed. 2), pp 389) using the statistical package S-Plus 6.1 (Insightful Inc., Seattle, Wash.). The size of the test was set at P=0.05.

EXAMPLE 9

Fluorescence In Situ Hybridization (FISH)

FISH analysis was performed using paraffin-embedded tissue sections from transgenic cyclin E and control mice. These studies were conducted according to the manufacturer's recommended procedures (Vysis, Des Plaines, Ill.). Murine chromosome 4 and 6 specific probes were purchased (Vysis, Des Plaines, Ill.) and independently used in these analyses.

EXAMPLE 10

Reverse Transcription-Polymerase Chain Reaction

Total cellular RNA was isolated using the RNEASY Protect Mini Kit (QIAGEN, Valencia, Calif.) or TRI Reagent (Molecular Research Center, Cincinnati, Ohio). Contaminating DNA was removed using a DNA-free kit according to the manufacturer's procedures (Ambion, Austin, Tex.). Reverse transcription (RT)-PCR assays were performed using previously established methods (Ma, et al. (2005) supra). The optimal PCR cycle number was determined. PCR products were detected using previously described methods (Ma, et al. (2005) supra). The primers used for RT-PCR assays were: forward primer for murine Smo 5'-AGA TTG TTT GCC GAG CAG AT-3' (SEQ ID NO:6); and reverse primer for murine Smo 5'-GTG AGG ACA AAG GGG AGT GA-3' (SEQ ID NO:7); forward primer for murine Gli1 5'-CCT GGT GGC TTT CAT CAA CT-3' (SEQ ID NO:8); and reverse primer for murine Gli1 5'-GCT AGA CAT GTC CCC TTC CA-3' (SEQ ID NO:9); forward primer for Patched 1 (Ptch1) 5'-TAC GTG GAG GTG GTT CAT CA-3' (SEQ ID NO:10); reverse primer for Ptch1 5'-CCT GAG TTG TCG CAG CAT TA-3' (SEQ ID NO:11); forward primer for murine glyceraldehyde-3-phosphate dehydrogenase (GAPDH) 5'-AAC TTT GGC ATT GTG GAA GG-3' (SEQ ID NO:12); reverse primer for murine GAPDH 5'-ACA CAT TGG GGG TAG GAA CA-3' (SEQ ID NO:13); forward primer for murine SHH 5'-TTA AAT GCC TTG GCC ATC TC-3' (SEQ ID NO:14); and reverse primer for murine SHH 5'-CCA CGG AGT TCT CTG CTT TC-3' (SEQ ID NO:15).

What is claimed is:

1. A transgenic mouse whose genome contains a transgene comprising a nucleic acid encoding a cyclin E protein operably linked to a regulatory element comprising a lung-specific promoter so that cyclin E protein levels are elevated in the lung of the mouse thereby promoting lung carcinogenesis so that more than 30% of the transgenic mice develop lung tumors.

2. The transgenic mouse of claim 1, where the mouse is subject to a second stimulus which promotes lung carcinogenesis.

3. The transgenic mouse of claim 1, wherein the cyclin E protein exposed by the mouse is degradation resistant and further wherein about 50% of the transgenic mice develop lung tumors.

4. A cell or cell line isolated from the transgenic mouse of claim 1.

5. A method for identifying a therapeutic agent for the chemoprevention or treatment of lung cancer comprising
administering a test agent or combination of test agents to a transgenic mouse of claim 1 or claim 2, and
determining whether the signs or symptoms associated with lung cancer are prevented, delayed or treated in the transgenic mouse thereby identifying a therapeutic agent for the chemoprevention or treatment of lung cancer.

6. A method for identifying a therapeutic agent for the chemoprevention or treatment of lung cancer comprising
contacting the cell or cell line of claim 4 with a test agent or combination of test agents, and
determining whether the test agent decreases the expression or activity of cyclin E, Gli1 or Shh in the cell or cell line thereby identifying a therapeutic agent for the chemoprevention or treatment of lung cancer.

* * * * *

UNITED STATES PATENT AND TRADEMARK OFFICE
CERTIFICATE OF CORRECTION

PATENT NO.       : 7,586,022 B2
APPLICATION NO.  : 11/996003
DATED            : September 8, 2009
INVENTOR(S)      : Dmitrovsky et al.

Page 1 of 1

It is certified that error appears in the above-identified patent and that said Letters Patent is hereby corrected as shown below:

Title page, item [63] insert --Related U.S. Application Data Provisional Application No. 60/703,235 filed July 28, 2005--.

Signed and Sealed this

Twentieth Day of October, 2009

David J. Kappos
*Director of the United States Patent and Trademark Office*

```
                              SEQUENCE LISTING

<160> NUMBER OF SEQ ID NOS: 15

<210> SEQ ID NO 1
<211> LENGTH: 395
<212> TYPE: PRT
<213> ORGANISM: Homo sapiens

<400> SEQUENCE: 1

Met Lys Glu Asp Gly Gly Ala Glu Phe Ser Ala Arg Ser Arg Lys Arg
1               5                   10                  15

Lys Ala Asn Val Thr Val Phe Leu Gln Asp Pro Asp Glu Glu Met Ala
            20                  25                  30

Lys Ile Asp Arg Thr Ala Arg Asp Gln Cys Gly Ser Gln Pro Trp Asp
        35                  40                  45

Asn Asn Ala Val Cys Ala Asp Pro Cys Ser Leu Ile Pro Thr Pro Asp
    50                  55                  60

Lys Glu Asp Asp Arg Val Tyr Pro Asn Ser Thr Cys Lys Pro Arg
65                  70                  75                  80

Ile Ile Ala Pro Ser Arg Gly Ser Pro Leu Pro Val Leu Ser Trp Ala
                85                  90                  95

Asn Arg Glu Glu Val Trp Lys Ile Met Leu Asn Lys Glu Lys Thr Tyr
            100                 105                 110

Leu Arg Asp Gln His Phe Leu Glu Gln His Pro Leu Leu Gln Pro Lys
        115                 120                 125

Met Arg Ala Ile Leu Leu Asp Trp Leu Met Glu Val Cys Glu Val Tyr
    130                 135                 140

Lys Leu His Arg Glu Thr Phe Tyr Leu Ala Gln Asp Phe Phe Asp Arg
145                 150                 155                 160

Tyr Met Ala Thr Gln Glu Asn Val Val Lys Thr Leu Leu Gln Leu Ile
                165                 170                 175

Gly Ile Ser Ser Leu Phe Ile Ala Ala Lys Leu Glu Glu Ile Tyr Pro
            180                 185                 190

Pro Lys Leu His Gln Phe Ala Tyr Val Thr Asp Gly Ala Cys Ser Gly
        195                 200                 205

Asp Glu Ile Leu Thr Met Glu Leu Met Ile Met Lys Ala Leu Lys Trp
    210                 215                 220

Arg Leu Ser Pro Leu Thr Ile Val Ser Trp Leu Asn Val Tyr Met Gln
225                 230                 235                 240

Val Ala Tyr Leu Asn Asp Leu His Glu Val Leu Leu Pro Gln Tyr Pro
                245                 250                 255

Gln Gln Ile Phe Ile Gln Ile Ala Glu Leu Leu Asp Leu Cys Val Leu
            260                 265                 270

Asp Val Asp Cys Leu Glu Phe Pro Tyr Gly Ile Leu Ala Ala Ser Ala
        275                 280                 285
```

```
Leu Tyr His Phe Ser Ser Glu Leu Met Gln Lys Val Ser Gly Tyr
    290                 295                 300
Gln Trp Cys Asp Ile Glu Asn Cys Val Lys Trp Met Val Pro Phe Ala
305                 310                 315                 320
Met Val Ile Arg Glu Thr Gly Ser Ser Lys Leu Lys His Phe Arg Gly
                325                 330                 335
Val Ala Asp Glu Asp Ala His Asn Ile Gln Thr His Arg Asp Ser Leu
            340                 345                 350
Asp Leu Leu Asp Lys Ala Arg Ala Lys Lys Ala Met Leu Ser Glu Gln
        355                 360                 365
Asn Arg Ala Ser Pro Leu Pro Ser Gly Leu Leu Thr Pro Pro Gln Ser
    370                 375                 380
Gly Lys Lys Gln Ser Ser Gly Pro Glu Met Ala
385                 390                 395

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 2
aagtgctact gccgcagtat c                                            21

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 3
cagtggtgcg acatagagaa c                                            21

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
ttatctgggc ttcggttctg                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
tcgattttgg ccatttcttc                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
```
agattgtttg ccgagcagat                                                    20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
gtgaggacaa aggggagtga                                                    20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
cctggtggct ttcatcaact                                                    20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
gctagacatg tccccttcca                                                    20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
tacgtggagg tggttcatca                                                    20

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
cctgagttgt cgcagcatta                                                    20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
aactttggca ttgtggaagg                                                    20

<210> SEQ ID NO 13
<211> LENGTH: 20
<212> TYPE: DNA

```
<213> ORGANISM: Artificial Sequence
<220> FEATURE:
<223> OTHER INFORMATION: Synthetic oligonucleotide

<400> SEQUENCE: 13
acacattggg ggtaggaaca                                                    20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
ttaaatgcct tggccatctc                                                    20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
ccacggagtt ctctgctttc                                                    20
```